(12) United States Patent
Qiu et al.

(10) Patent No.: US 10,729,624 B2
(45) Date of Patent: Aug. 4, 2020

(54) HIGH-ULTRAVIOLET ABSORPTION LIGNIN/CHEMICAL SUN-SCREENING AGENT MICROCAPSULE AND PREPARATION METHOD THEREFOR

(71) Applicant: SOUTH CHINA UNIVERSITY OF TECHNOLOGY, Guangzhou (CN)

(72) Inventors: Xueqing Qiu, Guangzhou (CN); Yong Qian, Guangzhou (CN); Ying Li, Guangzhou (CN); Dongjie Yang, Guangzhou (CN); Hongming Lou, Guangzhou (CN); Shiping Zhu, Guangzhou (CN); Weifeng Liu, Guangzhou (CN)

(73) Assignee: SOUTH CHINA UNIVERSITY OF TECHNOLOGY, Guangzhou, Guangdong (CN)

( * ) Notice: Subject to any disclaimer, the term of this patent is extended or adjusted under 35 U.S.C. 154(b) by 0 days.

(21) Appl. No.: 16/322,444

(22) PCT Filed: Nov. 21, 2017

(86) PCT No.: PCT/CN2017/112098
§ 371 (c)(1),
(2) Date: Jan. 31, 2019

(87) PCT Pub. No.: WO2018/099297
PCT Pub. Date: Jun. 7, 2018

(65) Prior Publication Data
US 2019/0343736 A1    Nov. 14, 2019

(30) Foreign Application Priority Data
Dec. 2, 2016 (CN) .......................... 2016 1 1093275

(51) Int. Cl.
| | | |
|---|---|---|
| *A61K 8/11* | (2006.01) | |
| *A61K 8/9794* | (2017.01) | |
| *A61K 8/9789* | (2017.01) | |
| *A61K 8/35* | (2006.01) | |
| *A61K 8/37* | (2006.01) | |
| *A61Q 17/04* | (2006.01) | |
| *B01J 13/18* | (2006.01) | |

(52) U.S. Cl.
CPC ................. *A61K 8/11* (2013.01); *A61K 8/35* (2013.01); *A61K 8/37* (2013.01); *A61K 8/9789* (2017.08); *A61K 8/9794* (2017.08); *A61Q 17/04* (2013.01); *B01J 13/185* (2013.01)

(58) Field of Classification Search
CPC .................................... A61K 7/42; A61K 7/00
USPC ........................................................ 424/59
See application file for complete search history.

(56) References Cited

U.S. PATENT DOCUMENTS

| 5,114,717 A * | 5/1992 | Kuznitz ............... A61K 8/0229 424/401 |
| 2002/0182155 A1* | 12/2002 | SenGupta ................ A61K 8/04 424/59 |
| 2006/0280702 A1 | 12/2006 | SenGupta et al. |
| 2007/0178057 A1 | 8/2007 | SenGupta et al. |

FOREIGN PATENT DOCUMENTS

| CN | 105163706 A | 12/2015 |
| CN | 106852724 A | 6/2017 |

OTHER PUBLICATIONS

Tortora et al., "Ultrasound Driven Assembly of Lignin into Microcapsules for Storage and Delivery of Hydrophobic Molecules." Biomacromolecules 2014, 15, 1634-1643. (Year: 2014).*
WIPO, Chinese International Search Authority, International Search Report and Written Opinion dated Feb. 24, 2018 in International Patent Application No. PCT/CN2017/112098, 10 pages.

* cited by examiner

*Primary Examiner* — Walter E Webb
(74) *Attorney, Agent, or Firm* — Masuvalley & Partners

(57) ABSTRACT

The present invention, belonging to the technical field of chemical sun-screening agent preparation, discloses a high-ultraviolet absorption lignin/chemical sun-screening agent microcapsule using lignin as a wall material and a preparation method therefor. The method of the present invention comprises the following steps: (1) dissolving 1-20 parts by weight of lignin in 100-200 parts by weight of an aqueous solution with a pH of 12, adjusting the pH of the solution to 7-10, and then removing insoluble substances by filtration to obtain a lignin solution; and (2) mixing 10-50 parts by weight of the lignin solution in step (1) with 1-10 parts by weight of a chemical sun-screening agent, and performing ultrasonic radiation under a power of 200-1500 W for 10 s to 25 min to obtain a lignin/chemical sun-screening agent microcapsule emulsion. The lignin/chemical sun-screening agent microcapsule of the present invention has excellent ultraviolet absorption performance, can avoid photodegradation of the chemical sun-screening agent, and has good stability; and it effectively prevents the chemical sun-screening agent from directly contacting and hurting the skin, having great application prospects in the field of sun-screening skincare products.

9 Claims, 2 Drawing Sheets

HIGH-ULTRAVIOLET ABSORPTION LIGNIN/CHEMICAL SUN-SCREENING AGENT MICROCAPSULE AND PREPARATION METHOD THEREFOR

RELATED APPLICATIONS

This application is the U.S. National Phase of and claims priority to International Patent Application No. PCT/CN2017/112098, International Filing Date Nov. 21, 2017, entitled High-Ultraviolet Absorption Lignin/Chemical Sun-Screening Agent Microcapsule And Preparation Method Therefor; which claims benefit of Chinese Application No. 201611093275.X filed Dec. 2, 2016; both of which are incorporated herein by reference in their entireties.

FIELD OF THE INVENTION

The present invention belongs to the technical field of chemical sun-screening agent preparation, and particularly relates to a high-ultraviolet absorption lignin/chemical sun-screening agent microcapsule using lignin as a wall material and a preparation method therefor.

BACKGROUND OF THE INVENTION

Sun exposure is one of the important factors that cause skin aging. Intense ultraviolet radiation may cause skin cancer. Studies have shown that ultraviolet rays in the UVB band (290-320 nm) can pass through the stratum corneum and epidermis, causing skin erythema, leading to DNA damage. Ultraviolet rays in the UVA band (320-400 nm) can reach the dermis and is an important factor in triggering melanoma. Therefore, effective sun protection is necessary. Sun-screening agents can effectively absorb or scatter ultraviolet rays in the UVB and UVA bands of sunlight, and are generally classified into two major categories: physical and chemical. Physical sun-screening agents such as titanium dioxide and zinc oxide and other inorganic particles can reflect or scatter ultraviolet radiation, but have poor affinity with the skin, easily accumulate on the hair follicle, and have poor comfort, which make them have certain limitations in practical applications. Therefore, the active ingredients in sun-screening skincare products are mainly chemical sun-screening agents.

The sun-screening skincare products based on the chemical sun-screening agents have more delicate texture, a relatively wide sun-screening spectrum and a relatively strong sun-screening ability, and are thus generally welcomed by consumers. However, the chemical sun-screening agent itself can absorb ultraviolet rays, has photochemical activity or physical activity, and undergoes photodegradation after absorbing ultraviolet rays, resulting in a decrease in the ability of the sun-screening agent to absorb ultraviolet rays, a poor sun-screening effect for a long time, and also an increase in irritation and allergy of the skin caused by the degradation products.

In addition, the chemical sun-screening agents are generally micromolecular compounds that can penetrate skin cells and trigger DNA variation, and are easy to have their molecular chains broken under illumination to produce highly active free radicals that can damage biological macromolecules and various cells and then lead to skin aging or skin cancer.

In order to solve the above problems, researchers at home and abroad have developed a variety of substrate systems such as liposomes and gels to coat the chemical sun-screening agents. The stability of the coated chemical sun-screening agents is greatly improved, and the chemical sun-screening agents can be isolated from the skin, reducing the toxic side effects on the skin. Liu Shuangxi and Song Chunjin developed a preparation method of a chemical sun-screening agent coated with chitosan gel as a wall material. First, gelatin, the chemical sun-screening agent and an emulsifier are emulsified at a high speed, and then a mixed solution of chitosan and acetic acid is added to the primary emulsion, followed by re-agglomeration with calcium chloride and curing with glutaraldehyde as a cross-linking agent to form a chemical sun-screening agent embedded body (CN 1709219 [P]). Zhang Wanping and Niu Wenxia effectively coated the octyl methoxycinnamate chemical sun-screening agent with solid lipid nanoparticles and inhibited the penetration of the chemical sun-screening agent into the skin by controlling the particle size of the coating carrier (Zhang Wanping, Niu Wenxia, *Preparation and characterization of solid lipid nanoparticles loaded octyl methoxycinnamate* [J], CIESC Journal, 2011, 62(10): 2965-2968). Deng et al. prepared polylactic acid-polyglycerol by multi-step synthesis for embedding a chemical sun-screening agent, and further hydroformylated polyglycerol to prepare polymer/chemical sun-screening agent microcapsules with bioadsorption properties (*Nature Materials*, 2015, 14: 1278-1285). Whether it is chitosan and liposome, or polylactic acid-polyglycerol by multi-step synthesis, although the chemical sun-screening agent can be embedded by chemical crosslinking, it is necessary to add various additives such as an emulsifier and a crosslinking agent. The addition of these additives not only increases the cost of preparation and separation, but also causes the hurt of the additive residue to the human body and skin. Besides, the embedding and retention properties of the above wall materials for the chemical sun-screening agent are yet to be further evaluated.

Lignin is a natural polymer compound widely present in the cell wall of plants. Many functional groups such as a benzene ring, a double bond, a carbonyl group and a phenolic hydroxyl group in the molecule of lignin determine that lignin can not only absorb ultraviolet rays, but also have the function of scavenging free radicals, and is thus a natural UV absorber and antioxidant. With lignin having excellent UV and oxidation resistance and good dispersibility, Qian et al. mixed alkali lignin with a hand cream without a sun-screening effect; when the lignin content was 10%, the sun-screening index (SPF value) of the mixed cream reached 5.72; when the alkali lignin was mixed with a commercially available sun-screening cream with an SPF of 15 and the amount of the alkali lignin was 2%, the SPF value of the mixed cream reached 35.32; and when the amount of the alkali lignin was 10%, the SPF value of the mixed cream even reached 89.58. These indicate that lignin not only has broad-spectrum UV protective properties, but also synergizes with chemical sun-screening agents in sun-screening creams (*Green Chemistry*, 2015, 17: 320-324).

Studies have shown that even industrial lignin is basically not cytotoxic and has good physiological compatibility after purification. These studies have largely eliminated the safety concerns of lignin in the cosmetic skincare field and even in the medical field (*Bioresources Technology*, 2008, 99(14): 6683-6687). Whether in terms of theory and experimentation, or in terms of ecology and safety, lignin can be developed into an anti-UV natural polymer wall material used to embed chemical sun-screening agents to prepare composite microcapsules, and is used in the field of sun-screening skincare.

CONTENTS OF THE INVENTION

In order to overcome the above shortcomings and disadvantages of the prior art, it is a primary object of the present invention to provide a high-ultraviolet absorption lignin/chemical sun-screening agent microcapsule using lignin as a wall material. The lignin/chemical sun-screening agent microcapsule of the present invention, having an amphiphilic spherical structure, has better ultraviolet absorption performance than the chemical sun-screening agent and lignin, can avoid photodegradation of the chemical sun-screening agent, and has good stability.

Another object of the present invention is to provide a method for preparing the above lignin/chemical sun-screening agent microcapsule.

Lignin has a large number of conjugated structures such as a benzene ring and a carbonyl group, as well as reactive functional groups with strong ultraviolet absorption such as a phenolic hydroxyl group and a methoxy group. The large number of phenolic hydroxyl groups present in the lignin molecule can form phenolic free radicals under ultrasonic radiation, which promote intermolecular cross-linking polymerization of lignin. The present invention combines a chemical sun-screening agent with a lignin solution, and prepares a lignin/chemical sun-screening microcapsule by one-step emulsion crosslinking by ultrasonic radiation. This method does not need to add an emulsifier or a cross-linking agent, has a simple preparation process and low cost, is environmentally friendly, and effectively expands the high-end and high-value application fields of the natural polymer lignin, and also effectively prevents the chemical sun-screening agent from contacting and hurting the skin, having great application prospects in the field of sun-screening skincare products.

The objects of the present invention are achieved through the following technical solution:

A method for preparing a lignin/chemical sun-screening agent microcapsule comprises the following steps:

(1) dissolving 1-20 parts by weight of lignin in 100-200 parts by weight of an aqueous solution with a pH of 12, adjusting the pH of the solution to 7-10, and then removing insoluble substances by filtration to obtain a lignin solution; and (2) mixing 10-50 parts by weight of the lignin solution in step (1) with 1-10 parts by weight of a chemical sun-screening agent, and performing ultrasonic radiation under a power of 200-1500 W for 10 s to 25 min to obtain a lignin/chemical sun-screening agent microcapsule emulsion.

The lignin may be one of industrial lignins such as solvent-based lignin, enzymatic lignin, alkali lignin and lignosulfonate, or a mixture thereof.

The alkali lignin includes wood pulp alkali lignin, bamboo pulp alkali lignin, wheat straw pulp alkali lignin, reed pulp alkali lignin, bagasse pulp alkali lignin, alfalfa pulp alkali lignin, and cotton pulp alkali lignin.

The lignosulfonate includes bamboo pulp lignosulfonate, wheat straw pulp lignosulfonate, reed lignosulfonate, bagasse pulp lignosulfonate, alfalfa pulp lignosulfonate, and cotton pulp lignosulfonate.

Industrial lignins are mainly derived from the steamed or boiled wastewater of the paper pulping industry. Their physical and chemical properties vary greatly depending on the fiber raw materials, pulping process and extraction method, so their applications are also very diverse. Industrial lignins are usually divided into four categories: (1) Hydrolyzed lignin: Hydrolyzed lignin is a residue obtained by saccharification with an acid; it has poor solubility in water and a solvent, and has poor reaction performance; the hydrolyzed lignin has been mostly condensed, so it is mostly used as a fuel. (2) Alkali lignin: Alkali lignin mainly comes from waste liquid of alkaline pulping methods such as a sulfate method and an alkaloid method. (3) Lignosulfonate: Lignosulfonate is derived from sulfite pulping waste liquid, having good water solubility and wide application prospects. (4) Other lignins: Solvent-based lignin, enzymatic lignin and the like.

The chemical sun-screening agent may be at least one of isooctyl methoxycinnamate, avobenzone, homosalate, and other chemical sun-screening agents.

In order to further achieve the objects of the present invention, the mass fraction of the lignin in the aqueous solution in step (1) is preferably from 3% to 10%, and the pH of the solution is preferably adjusted to 8.5-9.5.

In order to further achieve the objects of the present invention, the pH of the solution in step (1) is preferably adjusted using a dilute acid solution, more preferably using a dilute hydrochloric acid solution.

In order to further achieve the objects of the present invention, the weight ratio of the lignin solution to the chemical sun-screening agent in step (2) is preferably from 1:1 to 10:1.

In order to further achieve the objects of the present invention, the power of the ultrasonic radiation in step (2) is preferably controlled to be 600-1000 W, and the time of the ultrasonic radiation is preferably controlled to be 1-12 min.

In order to further achieve the objects of the present invention, the obtained lignin/chemical sun-screening agent microcapsule emulsion can be washed by centrifugation to remove excess lignin to obtain the lignin/chemical sun-screening agent microcapsule.

The rate of centrifugation is preferably 5,000-50,000 r/min, and the time of centrifugal washing is preferably 5-30 min.

The rate of centrifugation is more preferably 10,000 r/min, and the time of centrifugal washing is preferably 10-20 min.

The present invention provides a lignin/chemical sun-screening agent microcapsule prepared by the above method. The lignin/chemical sun-screening agent microcapsule of the present invention, having an amphiphilic spherical structure, has better ultraviolet absorption performance than the chemical sun-screening agent and lignin, can avoid photodegradation of the chemical sun-screening agent, and has good stability.

Lignin has a large number of conjugated structures such as a benzene ring and a carbonyl group, as well as reactive functional groups with strong ultraviolet absorption such as a phenolic hydroxyl group and a methoxy group. The large number of phenolic hydroxyl groups present in the lignin molecule can form phenolic free radicals under ultrasonic radiation, which promotes intermolecular cross-linking polymerization of lignin. The present invention combines a chemical sun-screening agent with a lignin solution, and prepares a lignin/chemical sun-screening microcapsule by one-step emulsion crosslinking by ultrasonic radiation. This method does not need to add an emulsifier or a cross-linking agent, has a simple preparation process and low cost, is environmentally friendly, and effectively expands the high-end and high-value application fields of the natural polymer lignin, and also effectively prevents the chemical sun-screening agent from contacting and hurting the skin, having great application prospects in the field of sun-screening skincare products.

Compared with the prior art, the present invention has the following advantages and beneficial effects:

1. The present invention utilizes abundant lignin as a wall material to embed the chemical sun-screening agent without additionally adding an emulsifier or a cross-linking agent, adopts ultrasonic radiation to emulsify cross-linking, and obtains the lignin/chemical sun-screening agent microcapsule in one step. The preparation process is simple and environmentally friendly, the cost is low, and functional structures such as phenolic hydroxyl groups of lignin that enhance UV absorption and oxidation resistance are also retained.

2. The wall material of the lignin/chemical sun-screening agent microcapsule of the present invention is amphiphilic lignin that has good compatibility with the water-based and oil-based cream systems. The synergistic effect produced by the lignin and the chemical sun-screening agent can further enhance the UV protection effect. The lignin microcapsules can well maintain the embedded chemical sun-screening agent for long-lasting sun protection, and have a good market potential in the field of sun-screening skincare.

3. The lignin used in the present invention is derived from a plant and coexists with human beings, and the natural molecular structure of the polymer makes it have good photostability. As a wall material, the lignin can prevent chemical sun-screening agents not only from being degraded by sunlight but also from contacting and hurting the skin, while the lignin itself has no toxic side effects.

DETAILED DESCRIPTION OF THE EMBODIMENTS

The present invention will be further described in detail with reference to examples, but the embodiments of the present invention are not limited thereto.

The reagents used in the following examples are commercially available.

Example 1

(1) 20 g of solvent-based lignin was placed in a 500 mL beaker, 180 g of an aqueous solution of pH 12 was added to dissolve the lignin, and then diluted hydrochloric acid was added to adjust the pH of the solution to 8.5, and insolubles were filtered off to obtain a solvent-based lignin aqueous solution.

(2) 100 g of the chemical sun-screening agent homosalate was added to 100 g of the lignin solution obtained in step (1) at a water-oil ratio of 1:1, and the mixture was treated with ultrasonic radiation of 600 W for 12 min to obtain a lignin/homosalate microcapsule emulsion.

Figure 1:
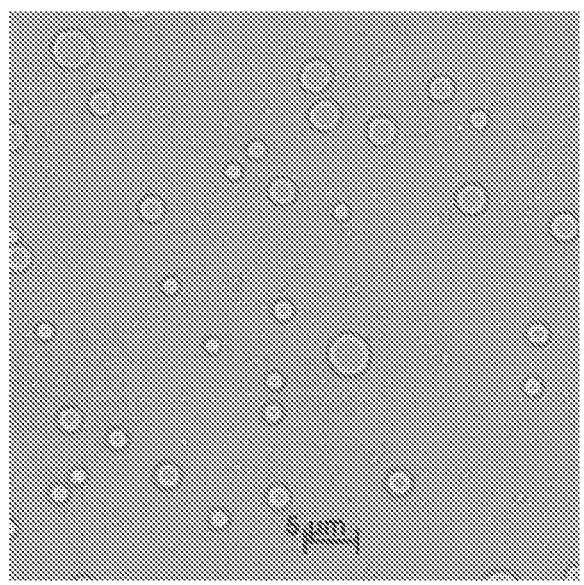
FIG. 1 shows an optical micrograph of the lignin/chemical sun-screening agent microcapsule of Example 1.

(3) The emulsion obtained in step (2) was centrifugally washed at 10,000 r/min for 20 min to obtain a lignin/homosalate microcapsule paste. FIG. 1 is an optical micrograph of the lignin/homosalate microcapsule product of Example 1 observed by an optical microscope, showing that the microcapsule had a spherical structure with a diameter less than 5 μm.

Figure 2:
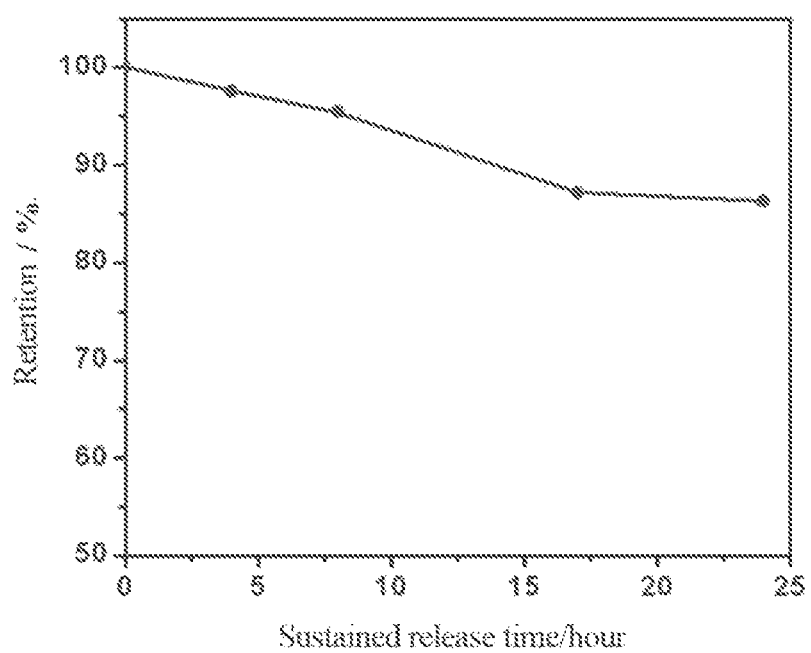
FIG. 2 shows a graph of the sustained release of the lignin/chemical sun-screening agent microcapsule of Example 1 in artificial sweat.

(4) The lignin/homosalate microcapsules obtained in step (3) were uniformly dispersed in ultrapure water, and then placed in a microdialysis tube with a molecular weight of 10,000, and subjected to a sustained release test in artificial sweat at a constant temperature of 35° C. The UV absorbance of the dispersion at 325 nm was measured by a Shimadzu UV-2450 UV-VIS spectrophotometer of Japan, and the release amount of the sun-screening agent was calculated. FIG. 2 is a graph of the sustained release of the lignin/homosalate microcapsule product of Example 1. It can be seen that the cumulative release of the chemical sun-screen agent, homosalate, of the product of Example 1 in the artificial sweat is only 15% at 35° C. after 24 h, indicating that the lignin/homosalate microcapsules can well embed and maintain the chemical sun-screening agent, and in turn can extend the UV absorption time.

Figure 3:
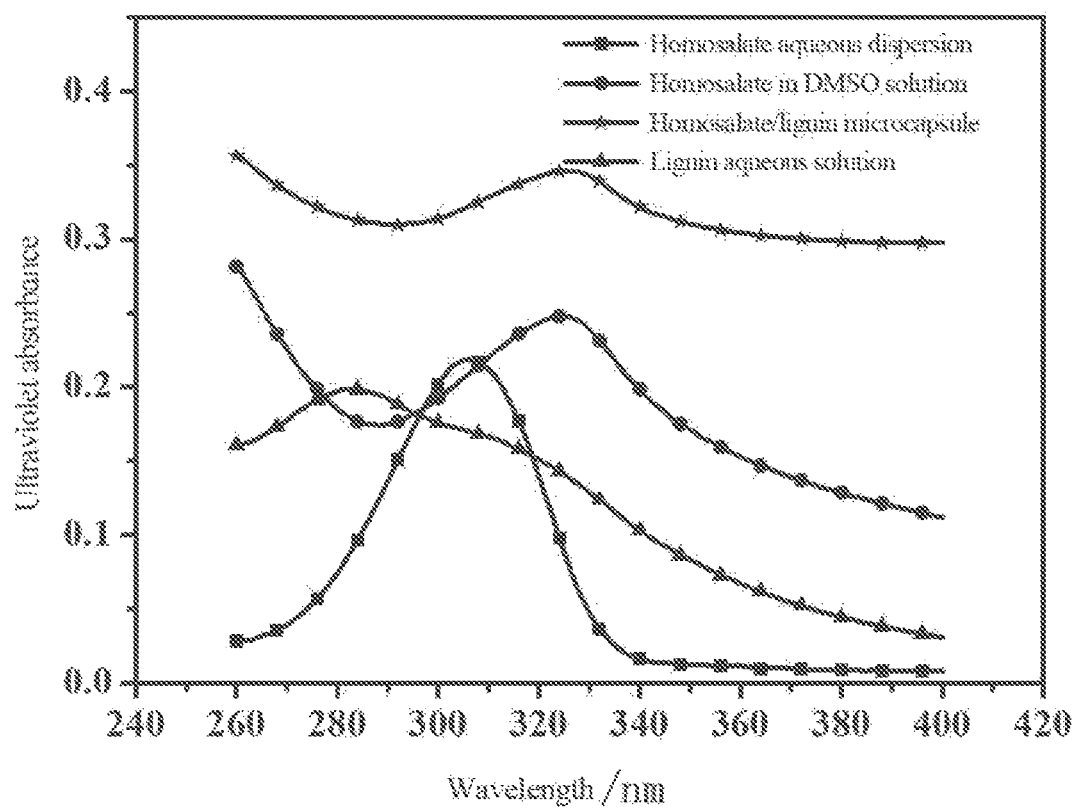
FIG. 3 shows a UV spectrum of the lignin, chemical sun-screening agent, and lignin/chemical sun-screening agent microcapsule of Example 1 in the range of 260-400 nm.

(5) The lignin/homosalate microcapsules obtained in step (3) were diluted to 0.01 mg/mL with ultrapure water, and a solvent-based lignin aqueous solution, an aqueous dispersion of the chemical sun-screening agent homosalate and a homosalate in DMSO solution having the same concentration were prepared and subjected to the ultraviolet absorbance test. FIG. 3 is a UV spectrum of the product of Example 1 and the samples of the lignin and chemical sun-screening agent measured by the Shimadzu UV-2450 UV-VIS spectrophotometer of Japan in the range of 260-400 nm. As can be seen from the figure, the UV absorbance of the lignin/homosalate microcapsule product of Example 1 is 2 to 3 times higher than the UV absorbance of the aqueous solutions of the enzymatic lignin and the sun-screening agent homosalate having the same concentration. The synergistic sun-screening effect of the lignin and the chemical sun-screening agent is proportional to the contact rate between the two. In the microcapsule system, the lignin is completely in contact with the chemical sun-screening agent homosalate, and the synergistic effect is more significant, which makes the UV absorption effect of the microcapsule product greatly improved.

Example 2

(1) 6 g of enzymatic lignin was placed in a 500 mL beaker, 194 g of an aqueous solution of pH 12 was added to dissolve the lignin, and then diluted hydrochloric acid was added to adjust the pH of the solution to 9.5, and insolubles were filtered off to obtain an enzymatic lignin aqueous solution having a mass fraction of 3%.

(2) 5 g of the chemical sun-screening agent isooctyl methoxycinnamate was added to 50 g of the lignin solution obtained in step (1) at a water-oil ratio of 10:1, and the mixture was treated with ultrasonic radiation of 1000 W for 1 min to obtain a lignin/isooctyl methoxycinnamate microcapsule emulsion.

(3) The emulsion obtained in step (2) was centrifugally washed at 10,000 r/min for 10 min to obtain a lignin/isooctyl methoxycinnamate microcapsule paste.

(4) The same optical microscope measurement, sustained-release analysis, and ultraviolet spectrum measurement as in Example 1 were carried out, with the results substantially the same as those in FIGS. 1-3, respectively.

Example 3

(1) 10 g of alkali lignin was placed in a 500 mL beaker, 190 g of an aqueous solution of pH 12 was added to dissolve the lignin, and then diluted hydrochloric acid was added to adjust the pH of the solution to 9.0, and insolubles were filtered off to obtain an alkali lignin aqueous solution having a mass fraction of 5%.

(2) 25 g of the chemical sun-screening agent of a mixture of homosalate and avobenzone was added to 50 g of the lignin solution obtained in step (1) at a water-oil ratio of 2:1, and the resulted mixture was treated with ultrasonic radiation of 800 W for 8 min to obtain a lignin/(homosalate and avobenzone) chemical sun-screening agent microcapsule emulsion.

(3) The emulsion obtained in step (2) was centrifugally washed at 10,000 r/min for 10 min to obtain a lignin/chemical sun-screening agent microcapsule paste.

(4) The same optical microscope measurement, sustained-release analysis, and ultraviolet spectrum measurement as in Example 1 were carried out, with the results substantially the same as those in FIGS. 1-3, respectively.

Example 4

(1) 15 g of lignosulfonate was placed in a 500 mL beaker, 185 g of an aqueous solution of pH 12 was added to dissolve the lignin, and then diluted hydrochloric acid was added to adjust the pH of the solution to 9.0, and insolubles were filtered off to obtain an alkali lignin aqueous solution having a mass fraction of 7.5%.

(2) 25 g of the chemical sun-screening agent of a mixture of octyl methoxycinnamate and avobenzone was added to 75 g of the lignin solution obtained in step (1) at a water-oil ratio of 3:1, and the resulted mixture was treated with ultrasonic radiation of 900 W for 6 min to obtain a lignin/(octyl methoxycinnamate and avobenzone) chemical sun-screening agent microcapsule emulsion.

(3) The emulsion obtained in step (2) was centrifugally washed at 10,000 r/min for 10 min to obtain a lignin/chemical sun-screening agent microcapsule paste.

(4) The same optical microscope measurement, sustained-release analysis, and ultraviolet spectrum measurement as in Example 1 were carried out, with the results substantially the same as those in FIGS. 1-3, respectively.

Example 5

(1) 8 g of lignosulfonate was placed in a 250 mL beaker, 192 g of an aqueous solution of pH 12 was added to dissolve the lignin, and then diluted hydrochloric acid was added to adjust the pH of the solution to 9.1, and insolubles were filtered off to obtain an alkali lignin aqueous solution having a mass fraction of 4%.

(2) 40 g of the chemical sun-screening agent of a mixture of octyl methoxycinnamate, homosalate and avobenzone was added to 80 g of the lignin solution obtained in step (1) at a water-oil ratio of 4:1, and the resulted mixture was treated with ultrasonic radiation of 700 W for 9 min to obtain a lignin/(octyl methoxycinnamate, homosalate and avobenzone) chemical sun-screening agent microcapsule emulsion.

(3) The emulsion obtained in step (2) was centrifugally washed at 10,000 r/min for 10 min to obtain a lignin/chemical sun-screening agent microcapsule paste.

(4) The same optical microscope measurement, sustained-release analysis, and ultraviolet spectrum measurement as in Example 1 were carried out, with the results substantially the same as those in FIGS. 1-3, respectively.

The above examples are preferred embodiments of the present invention, but the embodiments of the present invention are not limited thereto, and any other alterations, modifications, substitutions, combinations and simplifications made without departing from the spirit and principle of the present invention should be all equivalent replacements and included in the scope of protection of the present invention.

The invention claimed is:

1. A method for preparing a lignin/chemical sun-screening agent microcapsule, comprising the following steps:
   (1) dissolving 1-20 parts by weight of lignin in 100-200 parts by weight of an aqueous solution with a pH of 12, adjusting the pH of the solution to 7-10, and then removing insoluble substances by filtration to obtain a lignin solution; and
   (2) mixing 10-50 parts by weight of the lignin solution in step (1) with 1-10 parts by weight of a chemical sun-screening agent, and performing ultrasonic radiation under a power of 200-1500 W for 10 s to 25 min to obtain a lignin/chemical sun-screening agent microcapsule emulsion;
   wherein the chemical sun-screening agent is at least one of isooctyl methoxycinnamate, avobenzone, or homosalate.

2. The method for preparing the lignin/chemical sun-screening agent microcapsule according to claim 1, wherein the lignin is one of solvent-based lignin, enzymatic lignin, alkali lignin and lignosulfonate, or a mixture thereof.

3. The method for preparing the lignin/chemical sun-screening agent microcapsule according to claim 2, wherein the alkali lignin includes wood pulp alkali lignin, bamboo pulp alkali lignin, wheat straw pulp alkali lignin, reed pulp alkali lignin, bagasse pulp alkali lignin, alfalfa pulp alkali lignin, and cotton pulp alkali lignin; and
   the lignosulfonate includes bamboo pulp lignosulfonate, wheat straw pulp lignosulfonate, reed lignosulfonate, bagasse pulp lignosulfonate, alfalfa pulp lignosulfonate, and cotton pulp lignosulfonate.

4. The method for preparing the lignin/chemical sun-screening agent microcapsule according to claim 1, wherein the lignin in step (1) has a mass fraction of 3% to 10% in the aqueous solution.

5. The method for preparing the lignin/chemical sun-screening agent microcapsule according to claim 1, wherein the adjusting the pH of the solution in step (1) means adjusting the pH to 8.5-9.5.

6. The method for preparing the lignin/chemical sun-screening agent microcapsule according to claim 1, wherein the weight ratio of the lignin solution to the chemical sun-screening agent in step (2) is from 1:1 to 10:1.

7. The method for preparing the lignin/chemical sun-screening agent microcapsule according to claim 1, wherein the power of the ultrasonic radiation in step (2) is 600-1000 W.

8. The method for preparing the lignin/chemical sun-screening agent microcapsule according to claim 1, wherein the time of the ultrasonic radiation in step (2) is 1-12 min.

9. A lignin/chemical sun-screening agent microcapsule prepared by the method according to claim 1.

* * * * *